(12) United States Patent
Mofakhami et al.

(10) Patent No.: US 10,429,351 B2
(45) Date of Patent: Oct. 1, 2019

(54) HEALTH MONITORING OF COMPOSITE STRUCTURES

(71) Applicant: Bombardier Inc., Dorval (CA)

(72) Inventors: Mohammad Reza Mofakhami, Pointe-Claire (CA); Jerome Pinsonnault, Vaudreuil (CA); Alain Olsen, St-Lazare (CA)

(73) Assignee: BOMBARDIER INC., Dorval (CA)

( * ) Notice: Subject to any disclaimer, the term of this patent is extended or adjusted under 35 U.S.C. 154(b) by 112 days.

(21) Appl. No.: 15/034,368

(22) PCT Filed: Oct. 29, 2014

(86) PCT No.: PCT/IB2014/065689
§ 371 (c)(1),
(2) Date: May 4, 2016

(87) PCT Pub. No.: WO2015/068082
PCT Pub. Date: May 14, 2015

(65) Prior Publication Data
US 2016/0282308 A1    Sep. 29, 2016

Related U.S. Application Data

(60) Provisional application No. 61/901,672, filed on Nov. 8, 2013.

(51) Int. Cl.
*G01N 29/04* (2006.01)
*G01M 5/00* (2006.01)
(Continued)

(52) U.S. Cl.
CPC .......... *G01N 29/043* (2013.01); *B64D 45/00* (2013.01); *B64F 5/60* (2017.01); *G01M 5/0033* (2013.01);
(Continued)

(58) Field of Classification Search
CPC ...... G01N 29/043; G01N 29/04; G01N 29/12; G01N 29/348; G01N 29/11; G01N 29/28; G01N 29/265; G01N 29/225; G01N 29/46
See application file for complete search history.

(56) References Cited

U.S. PATENT DOCUMENTS 3,933,327 A * 1/1976 Cook ..................... B64D 15/04
244/134 B
5,841,031 A   11/1998 Chung
(Continued)

FOREIGN PATENT DOCUMENTS

CN    1693889 A    11/2005
CN    101755192 A    6/2010
(Continued)

OTHER PUBLICATIONS

PCT international Search Report and Written Opinion dated Feb. 2, 2015 re: International Application No. PCT/IB2014/065689.
(Continued)

Primary Examiner — Helen C Kwok
(74) Attorney, Agent, or Firm — Norton Rose Fulbright Canada LLP

(57) ABSTRACT

The present disclosure described devices, assemblies, apparatus and methods useful in conducting health monitoring of structures including monitoring for structural damage and liquid (e.g., water, fuel, anti-Icing fluid, moisture, etc.) Ingress in composite sandwich-type structures of mobile platforms. An exemplary method for detecting water Ingress in a structure comprises: introducing mechanical energy into the structure; sensing the mechanical energy transmitted through the structure; and determining the existence of water ingress in the structure based on the sensed mechanical energy.

21 Claims, 9 Drawing Sheets

(51) Int. Cl.
  B64D 45/00 (2006.01)
  G07C 5/00 (2006.01)
  B64F 5/60 (2017.01)
(52) U.S. Cl.
  CPC .......... *G01M 5/0066* (2013.01); *G01N 29/04* (2013.01); *G07C 5/008* (2013.01); *B64D 2045/0085* (2013.01); *G01N 2291/0231* (2013.01); *G01N 2291/0289* (2013.01); *G01N 2291/048* (2013.01); *G01N 2291/2694* (2013.01)

(56) References Cited

U.S. PATENT DOCUMENTS

| | | | | |
|---|---|---|---|---|
| 5,902,935 | A * | 5/1999 | Georgeson | G01N 29/2412 73/801 |
| 6,006,163 | A * | 12/1999 | Lichtenwalner | G01H 5/00 702/34 |
| 6,722,202 | B1 * | 4/2004 | Kennedy | G01N 29/225 73/634 |
| 6,734,982 | B2 * | 5/2004 | Banet | G01B 11/0666 356/432 |
| 6,743,504 | B1 * | 6/2004 | Allen | B29C 70/446 428/362 |
| 6,843,130 | B2 * | 1/2005 | Georgeson | G01N 29/11 73/600 |
| 7,010,982 | B2 | 3/2006 | Bergman | |
| 7,151,504 | B1 * | 12/2006 | Boatman | H01Q 1/422 343/872 |
| 7,313,959 | B2 * | 1/2008 | Georgeson | G01B 17/02 73/620 |
| 8,004,689 | B2 | 8/2011 | Monchalin et al. | |
| 8,176,785 | B2 | 5/2012 | David et al. | |
| 8,294,104 | B2 | 10/2012 | Dos Santos et al. | |
| 8,305,089 | B2 | 11/2012 | Dos Santos et al. | |
| 8,386,118 | B2 | 2/2013 | White et al. | |
| 8,499,632 | B1 | 8/2013 | Ihn et al. | |
| 8,694,269 | B2 * | 4/2014 | Mathews | G01M 5/0033 702/35 |
| 8,752,432 | B2 | 6/2014 | Meitzler et al. | |
| 9,709,457 | B2 | 7/2017 | Sugiyama et al. | |
| 2004/0103721 | A1 * | 6/2004 | Georgeson | G01N 29/11 73/599 |
| 2007/0005269 | A1 * | 1/2007 | Mitchell | G01B 11/162 702/35 |
| 2007/0166831 | A1 * | 7/2007 | Watkins, Jr. | G01N 27/041 436/149 |
| 2007/0199381 | A1 | 8/2007 | Volker | |
| 2009/0165392 | A1 * | 7/2009 | Totani | B60J 5/0401 49/502 |
| 2010/0024559 | A1 * | 2/2010 | Bossi | G01N 29/043 73/644 |
| 2011/0245999 | A1 * | 10/2011 | Kordonowy | G07C 5/0816 701/3 |
| 2012/0070668 | A1 * | 3/2012 | Georgeson | B29C 65/4855 428/411.1 |
| 2012/0265449 | A1 * | 10/2012 | Ihn | G01N 27/026 702/33 |
| 2013/0000408 | A1 | 1/2013 | Meitzler et al. | |
| 2013/0084422 | A1 * | 4/2013 | Thable | B64C 1/069 428/137 |
| 2013/0088724 | A1 * | 4/2013 | Dubois | G01H 9/00 356/519 |
| 2013/0147636 | A1 | 6/2013 | Georgeson et al. | |
| 2013/0174639 | A1 * | 7/2013 | Earthman | A61B 9/00 73/12.01 |
| 2013/0298690 | A1 * | 11/2013 | Bond | G01L 5/0052 73/788 |
| 2013/0320142 | A1 * | 12/2013 | Nordman | B64C 3/20 244/123.5 |
| 2015/0153313 | A1 * | 6/2015 | Kurashige | G01N 29/11 73/602 |
| 2017/0089866 | A1 * | 3/2017 | Kollgaard | G01N 29/043 |

FOREIGN PATENT DOCUMENTS

| | | |
|---|---|---|
| CN | 104280454 A | 1/2015 |
| JP | H05188041 | 7/1993 |

OTHER PUBLICATIONS

English translation of abstract of Japanese Publication No. JP H05 188041 dated Jul. 27, 1993.
English translation of Japanese Publication No. JP H05 188041 dated Jul. 27, 1993.
European Patent Office, Communication pursuant to Article 94(3) EPC dated Jan. 22, 2018 re: European patent application No. 14 802 193.4.
The State Intellectual Property Office of the People's Republic of China; Notification of First Office Action dated Mar. 9, 2018 re: China patent application No. 201480060676.8.
English translation of China patent document No. CN104280454A dated Jan. 14, 2015, https://www38.orbit.com/?locale=en&ticket=a3677822-7b98-40cc-b8ab-f8a79a9e52f0#PatentDocumentPage, accessed on Apr. 18, 2018.
English translation of China patent document No. CN1693889A dated Nov. 9, 2005, https://www38.orbit.com/?locale=en&ticket=a3677822-7b98-40cc-b8ab-f8a79a9e52f0#PatentDocumentPage, accessed on Apr. 18, 2018.
English translation of China patent document No. CN101755192A dated Jun. 23, 2010, https://www38.orbit.com/?locale=en&ticket=a3677822-7b98-40cc-b8ab-f8a79a9e52f0#PatentDocumentPage, accessed on Apr. 18, 2018.

* cited by examiner

HEALTH MONITORING OF COMPOSITE STRUCTURES

CROSS-REFERENCE TO RELATED APPLICATION

This application is a national phase application under 35 U.S.C. 371 of International Patent Application No. PCT/IB2014/065689 filed on Oct. 29, 2014, which claims priority from U.S. Provisional Patent Application Ser. No. 61/901,672, filed on Nov. 8, 2013, the entire content of which is incorporated herein by reference.

TECHNICAL FIELD

The disclosure relates generally to health monitoring of structures including the detection of health conditions such as structural damage and liquid ingress in sandwich-type composite structures.

BACKGROUND OF THE ART

Mobile platforms such as aircraft commonly include multi-layer structures such as sandwich-type composite structures to form various structural portions of their frames. Such structures can comprise an alveolar or cellular structure forming an internal layer lined on each side with a skin. The cellular structure may have a honeycomb configuration and the skins may be made from an impermeable material.

In aeronautics and especially in the maintenance of aircraft, it can be important to detect the presence of water in such structures. The presence of water may be an indication that one of the skins has been damaged and can also affect the worthiness and the weight of the structures. Typically, the presence of water in sandwich-type composite structures is detected either by regular inspections during maintenance procedures or by visible signs of its presence. However, portions of such structures may not be visible and can require some disassembly in order to be inspected. Some current non-destructive inspection (NDI) methods for detection of water ingress in such structures are limited to cases where water has accumulated on the inspection side of the structure as in the case using conventional ultrasonic probes and/or can require significant disassembly of part(s) of the mobile platform to permit radiography inspection. Such disassembly may be relatively labor intensive and may increase the cost and the time requirements for inspection.

Improvement is therefore desirable.

SUMMARY

The disclosure relates generally to health monitoring of structures. For example, the disclosure describes devices, apparatus, assemblies and methods for conducting health monitoring of composite structures including the detection of health conditions such as structural damage and/or liquid (e.g., water, fuel, anti-icing fluid, moisture, etc.) ingress in sandwich-type composite structures. The disclosure also describes devices, apparatus, assemblies and methods for conducting acousto-ultrasonic (e.g., guided wave) inspection of composite structures.

In one aspect, the disclosure describes an assembly comprising:

a structure including: a sandwich portion comprising a first layer and a second layer separated by an intermediate region; and a first portion adjacent the sandwich portion and mechanically coupled to the first layer and to the second layer of the sandwich portion;

an actuator configured to introduce mechanical energy into the first portion of the structure for transmission into the first layer and into the second layer of the sandwich portion of the structure; and a sensor configured to sense the mechanical energy transmitted from the actuator through at least one of the first layer and the second layer.

The structure may comprises a second portion mechanically coupled to the at least one of the first layer and the second layer of the sandwich portion. The second portion may be mechanically coupled to the first layer and to the second layer of the sandwich portion.

The sandwich portion may define a path along which the mechanical energy introduced into the first portion can be transmitted to the second portion. The path may comprise a first path comprising the first layer and a second path comprising the second layer.

The sandwich portion may be disposed between the first portion and the second portion.

The first portion and the second portion may be respectively disposed on different sides of the sandwich portion.

The sensor may be configured to sense mechanical energy in the second portion.

The second portion may comprise a monolithic structure.

The first portion may comprise a monolithic structure.

The intermediate region may comprise a honeycomb structure.

At least one of the actuator and the sensor may comprise a piezoelectric transducer.

The actuator may be configured to introduce a mechanical wave into the first portion.

In another aspect, the disclosure describes mobile platforms including aircraft comprising assemblies as disclosed herein.

In another aspect, the disclosure describes a method for inspecting a sandwich portion of a structure comprising a first layer and a second layer separated by an intermediate region. The method comprises:

introducing mechanical energy into a first portion adjacent the sandwich portion and mechanically coupled to the first layer and to the second layer of the sandwich portion;

sensing the mechanical energy transmitted through at least one of the first layer and the second layer; and determining a health condition of the sandwich portion based on the sensed mechanical energy.

The mechanical energy may be sensed in a second portion adjacent the sandwich portion and mechanically coupled to the at least one of the first layer and of the second layer.

The health condition may comprise the presence of a foreign substance in the sandwich portion.

The health condition may comprise water ingress in the sandwich portion.

The mechanical energy introduced may comprise a mechanical wave.

The determination of the health condition may comprise comparing data representative of the sensed mechanical energy with baseline data associated with the sandwich portion in a healthy state.

The determination of the health condition may comprise identifying a difference in waveform characteristic between the data representative of the sensed mechanical energy and the baseline data.

The waveform characteristic may include at least one of amplitude, frequency, phase shift, time delay and wave distortion.

In another aspect, the disclosure describes a method for inspecting a sandwich portion of a structure comprising a first layer and a second layer separated by an intermediate region. The method comprises:

introducing mechanical energy into a first structural portion;

permitting transfer of the mechanical energy from the first structural portion to a second structural portion via the first layer and the second layer of the sandwich portion;

sensing the mechanical energy in the second structural portion; and determining a health condition of the sandwich portion based on the sensed mechanical energy.

The health condition may comprise the presence of a foreign substance in the sandwich portion.

The health condition may comprise water ingress in the sandwich portion.

The mechanical energy may comprise a mechanical wave.

The determination of the health condition may comprise comparing data representative of the sensed mechanical energy with baseline data associated with the sandwich portion in a healthy state.

The determination of the health condition may comprise identifying a difference in amplitude between the data representative of the sensed mechanical energy and the baseline data.

The health condition may be representative of water ingress when the amplitude of the sensed mechanical energy is lower than the amplitude of the baseline data.

In another aspect, the disclosure describes a method for detecting liquid ingress in a structure. The method comprises:

introducing mechanical energy into the structure;

sensing the mechanical energy transmitted through the structure; and determining the existence of liquid ingress in the structure based on the sensed mechanical energy.

The mechanical energy may comprise a mechanical wave.

Determining the existence of liquid ingress may comprise comparing data representative of the sensed mechanical energy with baseline data associated with the structure in a healthy state.

Determining the existence of liquid ingress may comprise identifying a difference in amplitude between the sensed mechanical energy and the baseline data.

In another aspect, the disclosure describes an apparatus for detecting liquid ingress in a structure. The apparatus comprises:

at least one actuator configured to introduce mechanical energy into the structure;

at least one sensor configured to sense the mechanical energy transmitted through the structure;

at least one processor;

a medium or media including machine-readable instructions executable by the at least one processor and configured to cause the at least one processor to: using data representative of the mechanical energy sensed by the sensor, generate one or more signals representative of liquid ingress in the structure based on the sensed mechanical energy.

The mechanical energy may comprise a mechanical wave.

The machine-readable instructions may be configured to cause the at least one processor to generate one or more signals for controlling the at least one actuator.

The machine-readable instructions may be configured to cause the at least one processor to compare the data representative of the mechanical energy sensed by the sensor with baseline data associated with the sandwich structure without liquid ingress.

At least one of the at least one actuator and the at least one sensor may comprise a piezoelectric transducer.

In various aspects, the disclosure describes mobile platforms including aircraft comprising apparatus as disclosed herein. For example, the disclosure describes health monitoring systems of mobile platforms comprising apparatus as disclosed herein.

In another aspect, the disclosure describes a device for monitoring a composite structure of a mobile platform. The device comprises:

at least one processor;

a medium or media including machine-readable instructions executable by the at least one processor and configured to cause the at least one processor to:

using data representative of mechanical energy sensed in the composite structure, determine whether liquid ingress exists in the composite structure; and conditioned upon liquid ingress existing in the composite structure, generate one or more signals representative of one or more preventive or corrective actions being required.

The data may be representative of mechanical energy transmitted through a portion of the composite structure.

The data may be representative of a mechanical wave transmitted through a first layer and a second layer of the composite structure.

The machine-readable instructions may be configured to cause the processor to monitor at least one trend in the sensed data.

The machine-readable instructions may be configured to cause the processor to generate the one or more signals representative of the one or more preventive or corrective actions being required based on the monitored trend in the sensed data.

The machine-readable instructions may be configured to cause the processor to compare the sensed data with baseline data associated with the composite structure in a healthy state.

The machine-readable instructions may be configured to cause the processor to associate the sensed data with positional information of the mobile platform.

The mobile platform may comprise an aircraft and the machine-readable instructions may be configured to cause the processor to associate the sensed data with flight data associated with the aircraft.

The machine-readable instructions may be configured to cause the processor to use data from a plurality of mobile platforms.

The apparatus may be off-board the mobile platform.

In various aspects, the disclosure describes ground stations comprising devices as disclosed herein.

In various aspects, the disclosure describes the use of acousto-ultrasonic (e.g., guided wave) inspection for the detection of liquid ingress in structures including sandwich-type structures.

In various aspects, the disclosure describes the use of acousto-ultrasonic (e.g., guided wave) inspection for the detection of water ingress in structures including sandwich-type structures.

Further details of these and other aspects of the subject matter of this application will be apparent from the detailed description and drawings included below.

DESCRIPTION OF THE DRAWINGS

Reference is now made to the accompanying drawings, in which.

DETAILED DESCRIPTION

Aspects of various embodiments are described through reference to the drawings.

The present disclosure describes devices, assemblies, apparatus and methods useful in conducting health monitoring of structures including composite sandwich-type structures. In various embodiments, the devices, assemblies, apparatus and methods disclosed herein may be used to monitor composite structures of one or more (e.g., including fleets) of mobile platforms (e.g., vehicles) such as aircraft, trains, ships, automobiles or other types of manned or unmanned vehicles. Such mobile platforms may include corporate, private, commercial or any other type of aircraft including narrow-body, twin engine jet airliners. For example, the devices, apparatus, assemblies and methods disclosed herein may be used for conducting health monitoring of structures including the detection of health conditions such as structural damage, liquid (e.g., water, fuel, anti-icing fluid, moisture, etc.) ingress in such structures and/or other anomalies associated with such structures. In various embodiments, the devices, apparatus, assemblies and methods disclosed may be configured for conducting acousto-ultrasonic (e.g., guided wave) inspection of structures. In various embodiments, the devices, apparatus, assemblies and methods disclosed herein may be useful in detecting water ingress in such structures.

Figure 1:
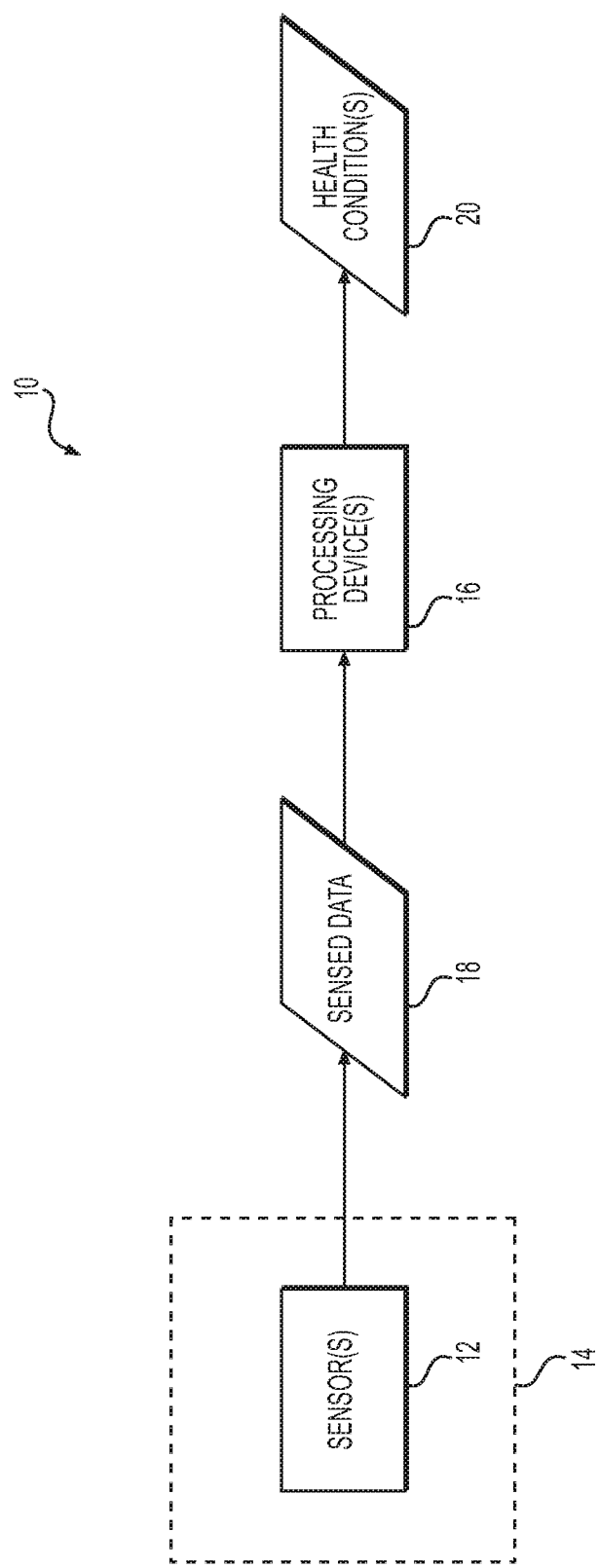
FIG. 1 shows a schematic representation of an exemplary apparatus for conducting structural health monitoring.

FIG. 1 shows a schematic representation of an exemplary apparatus, generally shown at 10, that may be used for structural health monitoring. Apparatus 10 may comprise one or more sensors 12 (referred hereinafter as "sensor 12") configured to acquire signals associated with one or more structures 14 (referred hereinafter as "structure 14"). Structure 14 may be part of a mobile platform. For example, structure 14 may be part of an aircraft such as a fuselage, fuel tank, wing, tail, stabilizer and/or flight control surface(s) of an aircraft. Accordingly, sensor 12 may be permanently coupled and secured to structure 14 or, alternatively, sensor 12 may be temporarily coupled to structure 14 for the purpose of acquisition of sensed data 18.

In various embodiments, sensor 12 may be configured to generate signals representative of sensed mechanical energy (e.g., mechanical wave(s), vibrations) in structure 14. For example, sensor 12 may comprise one or more piezoelectric transducers that may have the ability to sense mechanical waves in structure 14. As explained below, such mechanical waves may be generated using an actuator (see FIG. 2) associated with apparatus 10. Apparatus 10 may also comprise one or more processing devices 16 (referred hereinafter as "processing device 16"). Processing device 16 may be configured to receive one or more signals representative of sensed data 18 from sensor 12. Processing device 16 may be configured to generate one or more signals 20 representative of one or more health conditions (referred hereinafter as "generated signal 20") of structure 14 based on sensed data 18.

Processing device 16 may be located on-board or off-board the mobile platform to which structure 14 belongs. For example, processing device 16 may be part of a health monitoring system of the mobile platform (e.g., aircraft). Alternatively or in addition, processing device 16 may be part of ground support equipment (GSE) that may be configured for coupling with and receiving sensed data 18 from sensor 12 during inspection procedures conducted by maintenance personnel. For example, processing device 16 may be incorporated into a portable (e.g., hand-held) device, which may be coupled to sensor 12 via suitable wired and/or wireless interface(s). Alternatively, as explained further below, processing device 16 may be incorporated into a ground station and sensed data 18 may be transferred to processing device 16 via wired and/or wireless communication with one or more mobile platforms, manually by maintenance personnel or by other suitable (e.g., at least partially automated) means. Sensed data 18 may be received by processing device 16 at regular intervals, which may be predetermined.

Generated signal 20 may be representative of liquid (e.g., water, fuel, anti-icing fluid, moisture, etc.) ingress, structural damage, a level of structural damage or other (e.g., structural) anomaly(ies) associated with structure 14. It should be understood that the liquid could be in solid form (e.g., ice) during detection and that apparatus 10 may effectively be used to detect the presence of a foreign object or substance in structure 14. In the event of a detected health condition not being satisfactory, including the detection of liquid ingress, structural damage or other anomaly(ies) for example, generated signals 20 may be representative of (or reveal the need to conduct) one or more suggested, preventive or corrective actions. In the case where only a minor structural health issue is detected, a suggested action may be to modify an inspection schedule of structure 14 by increasing the inspection frequency for example. Alternatively, in the case where a more serious structural health issue is detected, suggested corrective or preventive actions may include an evaluation of structure 14 such as a visual inspection and/or a full integrity inspection of structure 14, repair and/or replacement of at least a portion of structure 14. Such preventive or corrective actions may then be scheduled and carried out by maintenance personnel. Alternatively, such preventive or corrective actions may comprise the activation of an alternate mode of operation of the mobile platform and/or the carrying out of an action by a system of the mobile platform to which structure 14 belongs. Such action(s) may be carried out automatically or semi-automatically by such system(s) of the mobile platform.

Figure 2:
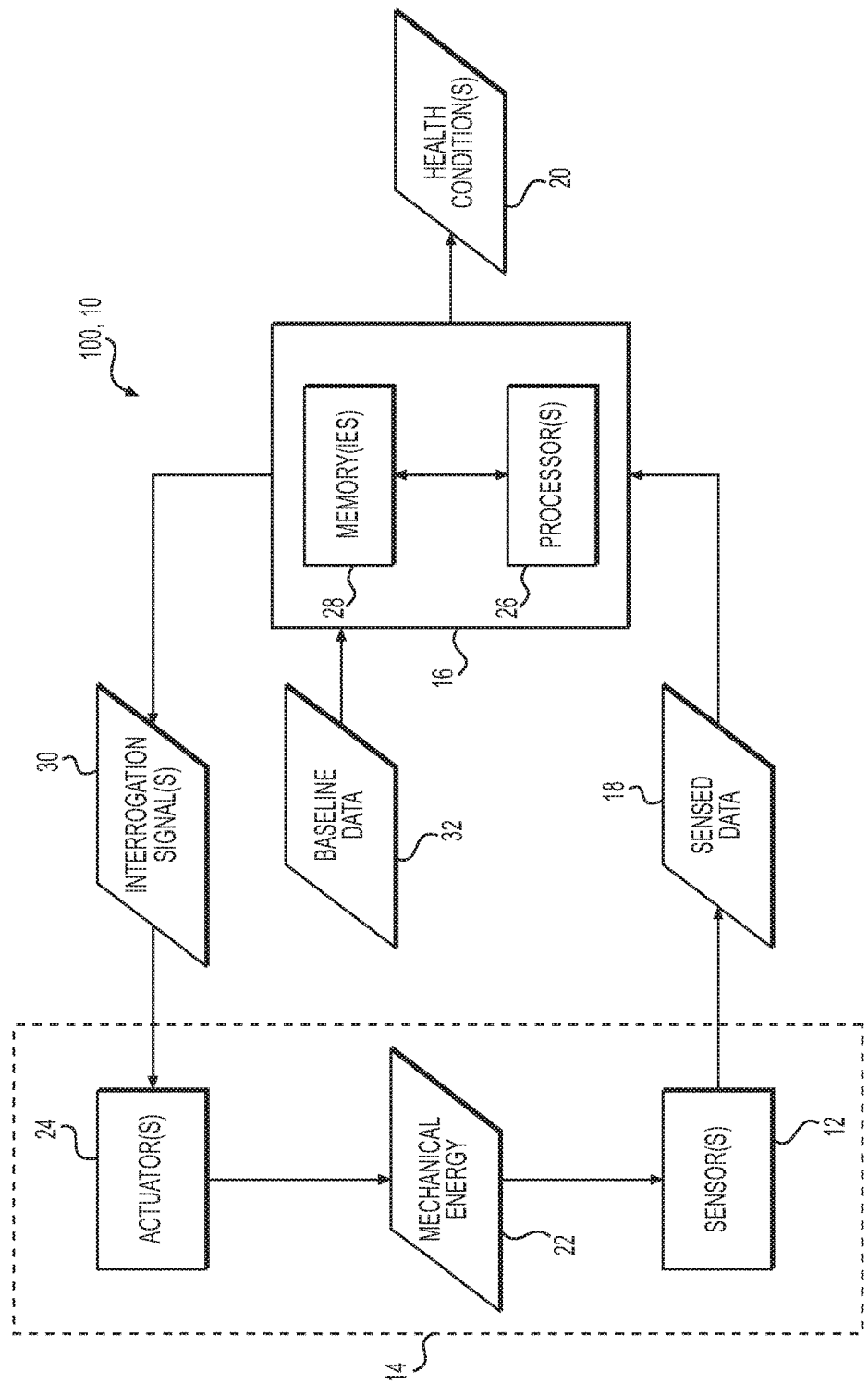
FIG. 2 shows another schematic representation of the apparatus of FIG. 1.

FIG. 2 shows a schematic representation of an apparatus, generally shown at 100, for health monitoring in accordance with another exemplary embodiment. Apparatus 100 may also be configured to output generated signal 20 representative of one or more health conditions associated with structure 14 based on sensed data 18. In various embodiments, apparatus 100 may be configured to carry-out acousto-ultrasonic (e.g., guided wave) inspection(s) of at least a portion of structure 14. For example, apparatus 100 may be configured to introduce mechanical energy 22 into structure 14 via one or more actuators 24. Some of mechanical energy 22 introduced by actuator 24 may be permitted to be transmitted through at least part of structure 14. For example, some mechanical energy 22 may be permitted to be transferred from actuator 24 to sensor 12 via one or more paths provided in structure 14 that may permit the transfer of mechanical energy 22 therealong. Accordingly, sensed data 18 may be representative of mechanical energy that has been transmitted through structure 14 from actuator 24. The transmission of mechanical energy through structure 14 may occur via direct transmission, reflection, refraction and/or diffraction.

Processing device 16 may comprise one or more digital computers or other data processors and related accessories for conducting at least some aspects of health monitoring of structure 14. For example, processing device 16 may comprise one or more processors 26 (hereinafter referred to as "processor 26"). Processor 26 may include one or more microcontrollers or other suitably programmed or programmable logic circuits. Processing device 16 may comprise one or more memories 28 (referred hereinafter as "memory 28") and memory data devices or registers. Memory 28 may comprise any storage means (e.g., devices) suitable for retrievably storing machine-readable data and instructions executable by processor 26. For example, memory 28 may include erasable programmable read-only memory (EPROM) and/or flash memory or other (e.g., electromagnetic) media suitable for storing electronic data signals in volatile or non-volatile, non-transient form. Memory 28 may contain machine-readable instructions for execution by processor 26. Such machine-readable instructions may cause processor 26 to output generated signal 20 based on sensed data 18. In various embodiments, generated signal 20 may be representative of a health condition such as liquid ingress in structure 14 and/or may be representative of one or more preventive or corrective actions being required or suggested with respect to structure 14.

Mechanical energy 22 may comprise one or more mechanical waves (e.g., vibrations) that is/are introduced into structure 14 by actuator 24. The mechanical wave(s) may be of a known waveform (e.g., amplitude, frequency and duration) and may be controllably generated by actuator 24. For example, processing device 16 may generate one or more interrogation signals 30 used to drive actuator 24 in order to introduce the desired mechanical wave(s) into structure 14. Accordingly, mechanical energy 22 may be selected based on one or more physical characteristics of structure 14 such as size, weight, configuration, shape, materials and/or natural frequency. Mechanical energy 22 may instead or in addition be selected based on the type of health condition (e.g., size of the structural damage) to be detected. In various embodiments, substantially the same mechanical waveform may be used repeatedly (e.g., periodically, pulsed or multi-cycle windowed toneburst) to interrogate structure 14 and monitor the structural health of structure 14.

In order to produce generated signal 20, sensed data 18 may be compared with baseline data 32. Baseline data 32 may be representative of an expected output from sensor 12 in response to the mechanical waveform introduced by actuator 24 when structure 14 is in a healthy state. For example, baseline data 32 may be generated by obtaining sensed data 18 in response to a known waveform being introduced by actuator 24 when structure 14 is healthy (e.g., free of substantial structural damage and/or liquid ingress) and then stored in memory 28 for future comparison(s). Then, for the purpose of inspection, the same waveform may be introduced by actuator 24 and sensed data 18 obtained from sensor 12 may be compared to baseline data 32 by comparing waveform characteristics. Differences in waveform characteristics between sensed data 18 and baseline data 32 may be indicative of one or more anomalies in structure 14. Such anomalies may include the presence of structural damage, a level or severity of structural damage and/or liquid ingress in structure 14. In various embodiments, processing device 16 may be configured to at least partially identify the type(s) of anomaly(ies) based on differences in waveform characteristics between sensed data 18 and baseline data 32.

In various embodiments, actuator 24 and sensor 12 may each comprise one or more piezoelectric transducers and may be of substantially identical construction. For example, each of actuator 24 and sensor 12 may be configured to transmit and/or sense mechanical energy. Accordingly, even though the exemplary embodiment shown in FIG. 2 shows mechanical energy 22 being transmitted from actuator 24 to sensor 12, it should be understood that transmission of the mechanical energy through structure 14 could also be carried out in the reverse direction.

Figure 3:
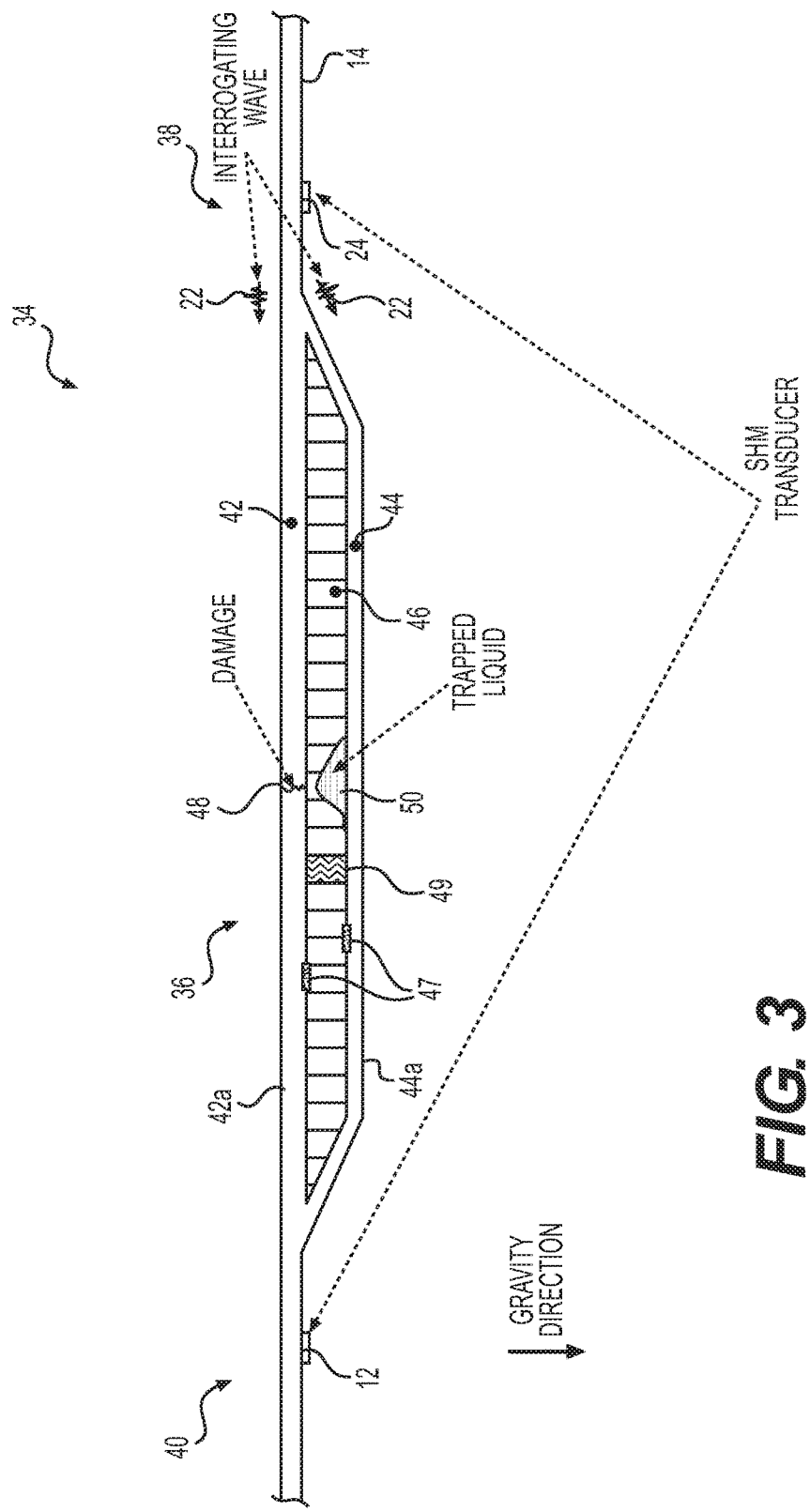
FIG. 3 shows a cross-sectional view of an assembly including a structure showing exemplary structural damage and liquid ingress.

FIG. 3 shows an assembly, generally shown at 34, including structure 14 (shown in cross-sectional view), actuator 24 and sensor 12. Structure 14 may comprise one or more composite materials. For example, one or more components of structure 14 may comprise carbon fiber reinforced plastic or other composite material suitable for aircraft applications. Structure 14 may comprise or form part of a fuselage and/or a tail portion of an aircraft. For example, structure 14 may be part of a fuselage crown or a horizontal stabilizer of an aircraft. Structure 14 may comprise sandwich portion 36, first portion 38 adjacent sandwich portion 36 and also second portion 40 adjacent sandwich portion 36. Actuator 24 may be operationally coupled to first portion 38 and sensor 12 may be operatively coupled to second portion 40. Alternatively or in addition, sensor 12 may be operatively coupled to a part of sandwich portion 36 of structure 14. It should be understood that one or more sensors 12 and/or one or more actuators 24 may be mounted to any suitable portion of structure 14. For example actuator 24 and/or sensor 12 may be permanently or temporarily operatively coupled to structure 14. The operative coupling of actuator 24 and sensor 12 to structure 14 may comprise mechanical coupling (e.g., securing) or other suitable type of coupling permitting the introduction of mechanical energy into structure 14 by actuator 24 and the sensing of mechanical energy 22 transmitted through structure 14 by sensor 12.

Sandwich portion 36 may comprise first layer 42 and second layer 44 separated by intermediate region 46. Intermediate region 46 may be substantially hollow or substantially filled. Intermediate region 46 may be otherwise known as a core of sandwich portion 36. For example, intermediate region 46 may comprise an alveolar or cellular structure that is lined on each side by first layer 42 and second layer 44. In other words, first layer 42 and second layer 44 may serve as skins lining each side of intermediate region 46. The cellular structure may have a honeycomb configuration and may be at least partially bonded to first layer 42 and/or second layer 44 by known or other means. One or more of first layer 42 and second layer 44 may be made of a substantially impermeable material. First layer 42 and second layer 44 may be made to meet (i.e., merge) on one or more sides of sandwich portion 36 in order to form an envelope around intermediate portion 46. For example, first layer 42 and second layer 44 may be made to meet in one or more of first portion 38 and second portion 40 of structure 14. Accordingly, first layer 42 and second layer 44 may be mechanically coupled to first portion 38. Similarly, first layer 42 and second layer 44 may be mechanically coupled to second portion 40. For example, first portion 38 and/or second portion 40 may comprise substantially solid (e.g., monolithic, solid laminate) structures. For example, first portion 38 and/or second portion 40 may comprise the merging of first layer 42 and second layer 44 to form a substantially solid structure without the honeycomb structure therebetween. First portion 38 and second portion 40 may be disposed on different sides of sandwich portion 36. For example, first portion 38 and second portion 40 may be disposed on opposite sides of sandwich portion 36 with sandwich portion 36 being disposed between first portion 38 and second portion 40.

The mechanical coupling of first layer 42 and second layer 44 to first portion 38 may permit mechanical energy 22 introduced by actuator 24 into first portion 38 to be transmitted through both first layer 42 and second layer 44. Similarly, the mechanical coupling of first layer 42 and second layer 44 to second portion 40 may permit mechanical energy 22 being transmitted through both first layer 42 and second layer 44 from first portion 38 to reach second portion 40. Accordingly, first layer 42 and second layer 44 may form one or more paths along which mechanical energy 22 may be transmitted from first portion 38 to second portion 40 and/or from second portion 40 to first portion 38. In other words, mechanical energy 22 introduced by actuator 24 may split between first layer 42 and second 44 as it is transmitted from first portion 38 and then re-combine when it reaches second portion 40 due to the merging of first layer 42 and second layer 44. It should be understood that some of the energy introduced by actuator 24 may be dissipated into structure 14 and also that some of the energy introduced by actuator 24 may be transmitted in directions other than toward sensor 12. Accordingly, it should be understood that only some of the mechanical energy introduced by actuator 24 may reach sensor 12.

First layer 42 of sandwich portion 36 may comprise an outer skin of structure 14. For example, first layer 42 may comprise outside surface 42a (opposite intermediate region 46), which may be exposed to the outside environment during use of a mobile platform to which structure 14 may belong. Second layer 44 may comprise an inner skin of structure 14. For example, second layer 44 may comprise inside surface 44a (opposite intermediate region 46), which may not be exposed to the outside environment during use of the mobile platform. FIG. 3 also shows exemplary structural damages 47, 48 and 49 that may be associated with structure 14 and that may be detectable using apparatus 10, 100. Structural damage 47 may, for example, comprise one or more disbonded regions between a cellular structure of intermediate region 46 and one or more of first layer 42 and second layer 44. Structural damage 48 may comprise one or more cracks, gouges, dents, holes or other type of undesirable structural damage in structure 14. Depending on its severity, structural damage 48 may cause liquid 50 (e.g., water) to penetrate first layer 42 and collect and get trapped in intermediate region 46. The presence of water or other liquid between first layer 42 and second layer 44 may be an undesirable health condition for structure 14. Structural damage 49 may comprise one or more portions of a core structure in intermediate region 46 that has been damaged (e.g., crushed). Accordingly, it may be desirable to detect one or more of such undesirable health conditions so that appropriate preventive and/or corrective action(s) may be carried out.

Depending on the specific configuration and orientation of structure 14, liquid 50 may collect on a surface which is not readily accessible for inspection using conventional forms on non-destructive inspection (NDI). For example, in the exemplary embodiment shown in FIG. 3, liquid 50 may collect against second layer 44 due to the orientation of structure 14 and the direction of the force of gravity. In the present example, second layer 44 may be an internal layer and inside surface 44a may not be visible or readily accessible to some conventional methods of non-destructive inspection (e.g., visual inspection, radiography, thermography) without some disassembly of part of the mobile platform. Otherwise, the use of some existing NDI methods on outside surface 42a only may not reveal the full extent of damage 48 and/or liquid ingress especially if, for example, liquid 50 has accumulated against second layer 44.

In various embodiments, the apparatus and methods disclosed herein may be used to detect structural damage 47, 48, 49, trapped liquid 50 and/or other foreign substance(s) with little to no disassembly of the mobile platform. For example, the transmission of mechanical energy 22 into second layer 44 may permit the inspection of second layer 44 even though second layer 44 may not be visible. Accordingly, the simultaneous transmission of mechanical energy 22 through first layer 42 and second layer 44 may permit the simultaneous inspection of first layer 42 and second layer 44. For example, such simultaneous inspection may permit the detection of anomalies (e.g., structural damage and/or water ingress) associated with either one or both of first layer 42 and second layer 44 without significant disassembly and may, in some cases, reduce the inspection times and costs compared to some other existing NDI methods.

Figure 4:
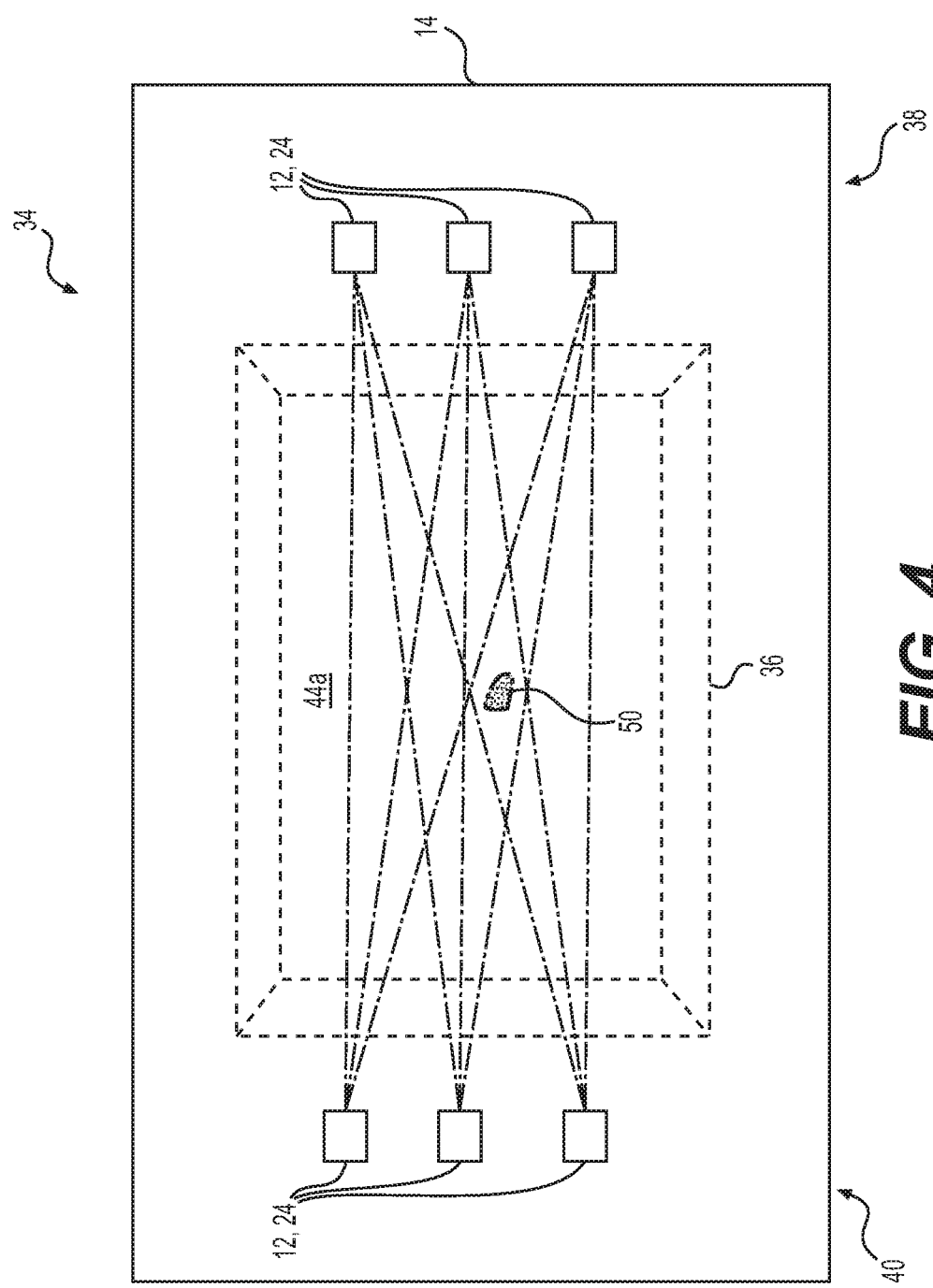
FIG. 4 shows a bottom view of the assembly of FIG. 3.

FIG. 4 shows a bottom view of assembly 34. Assembly 34 may comprise a plurality of actuators 24 and sensors 12 (e.g., a network of transducers 12, 24) that may be distributed to cover a desired area of structure 14. In various embodiments, actuators 24 and sensors 12 may be disposed on a surface of structure 14 (e.g., inside surface 44a) which is not directly exposed to the environment external to the mobile platform. For example, actuators/sensors 12, 24 may be arranged in the form of an array. For example one or more rows of actuators/sensors 12, 24 may be disposed in first portion 38 and one or more rows of actuators/sensors 12, 24 may be disposed in second portion 40. Stippled lines are shown between actuators/sensors 12, 24 disposed in first portion 38 and actuators/sensors 12, 24 disposed in second portion 40 to illustrate paths along which mechanical energy 22 may be transmitted across sandwich portion 36. The number of actuators/sensors 12, 24 may be selected based on the size of sandwich portion 36 and on the type of actuators/sensors 12, 24 selected. Actuators/sensors 12, 24 may be configured to be used in pairs (i.e., one from first portion 38 with one from second portion 40), in various combinations, or simultaneously all together. The use of a plurality of actuators 12 and sensors 24 may permit the identification of an approximate location and/or severity of damage 47, 48, 49 and/or liquid 50 in sandwich portion 36.

Figure 5:
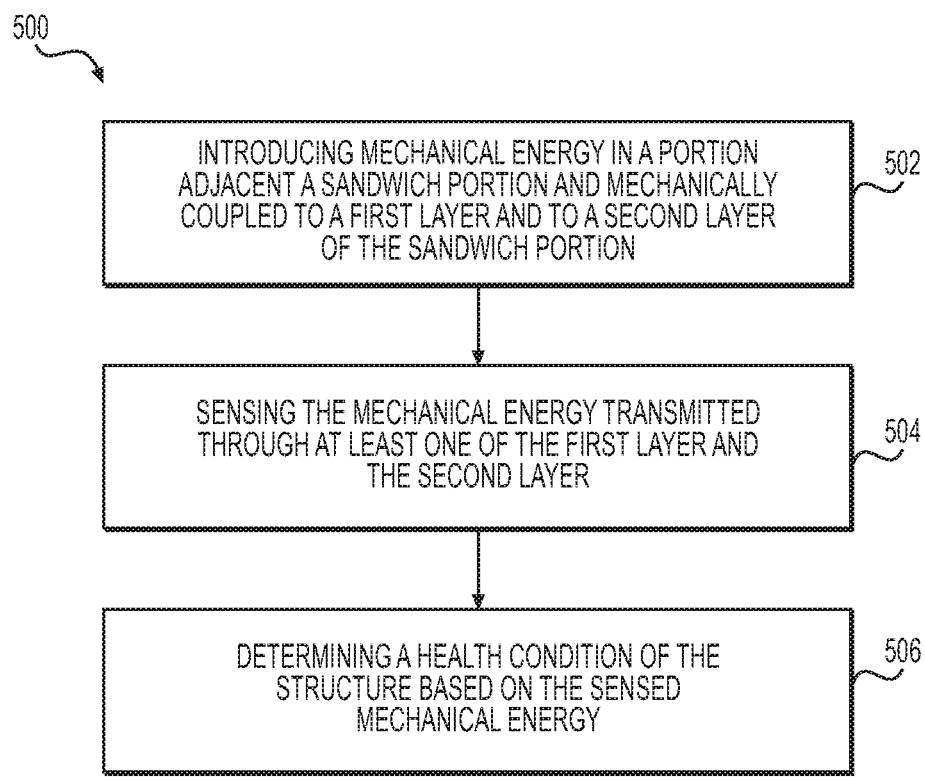
FIG. 5 shows a flowchart of a method for monitoring the health of a structure.

During operation, apparatus 10, 100 may be used to conduct health monitoring of structure 14. FIG. 5 shows a flowchart of an exemplary method 500 for monitoring sandwich portion 36 of structure 14 where structure 14 comprises first layer 42 and second layer 44 separated by intermediate region 46. Method 500 may comprise: introducing mechanical energy 22 into first portion 38 adjacent sandwich portion 36 and mechanically coupled to first layer 42 and to second layer 44 of sandwich portion 36 (see block 502); sensing mechanical energy 22 transmitted through at least one of first layer 42 and second layer 44 (see block 504); and determining health condition (e.g., generated signal 20) of sandwich portion 36 based on the sensed mechanical energy (see block 506).

Mechanical energy 22 may be sensed in second portion 40 adjacent sandwich portion 36 and mechanically coupled to the at least one of first layer 42 and of second layer 44. The health condition determined may comprise the presence of liquid/water 50 in sandwich portion 36, structural damage, a level of structural damage and/or other anomaly(ies) associated with structure 14. The health condition determined may also comprise a suggested increased inspection schedule, among other possibilities. For example, the health condition determined may comprise water ingress in sandwich portion 36. Mechanical energy 22 introduced into first portion 38 may comprise one or more mechanical waves of predetermined waveform(s). The determination of health condition may comprise comparing data representative of the sensed mechanical energy (e.g., sensed data 18) with baseline data 32 associated with sandwich portion 36 being in a healthy state.

Figure 6:
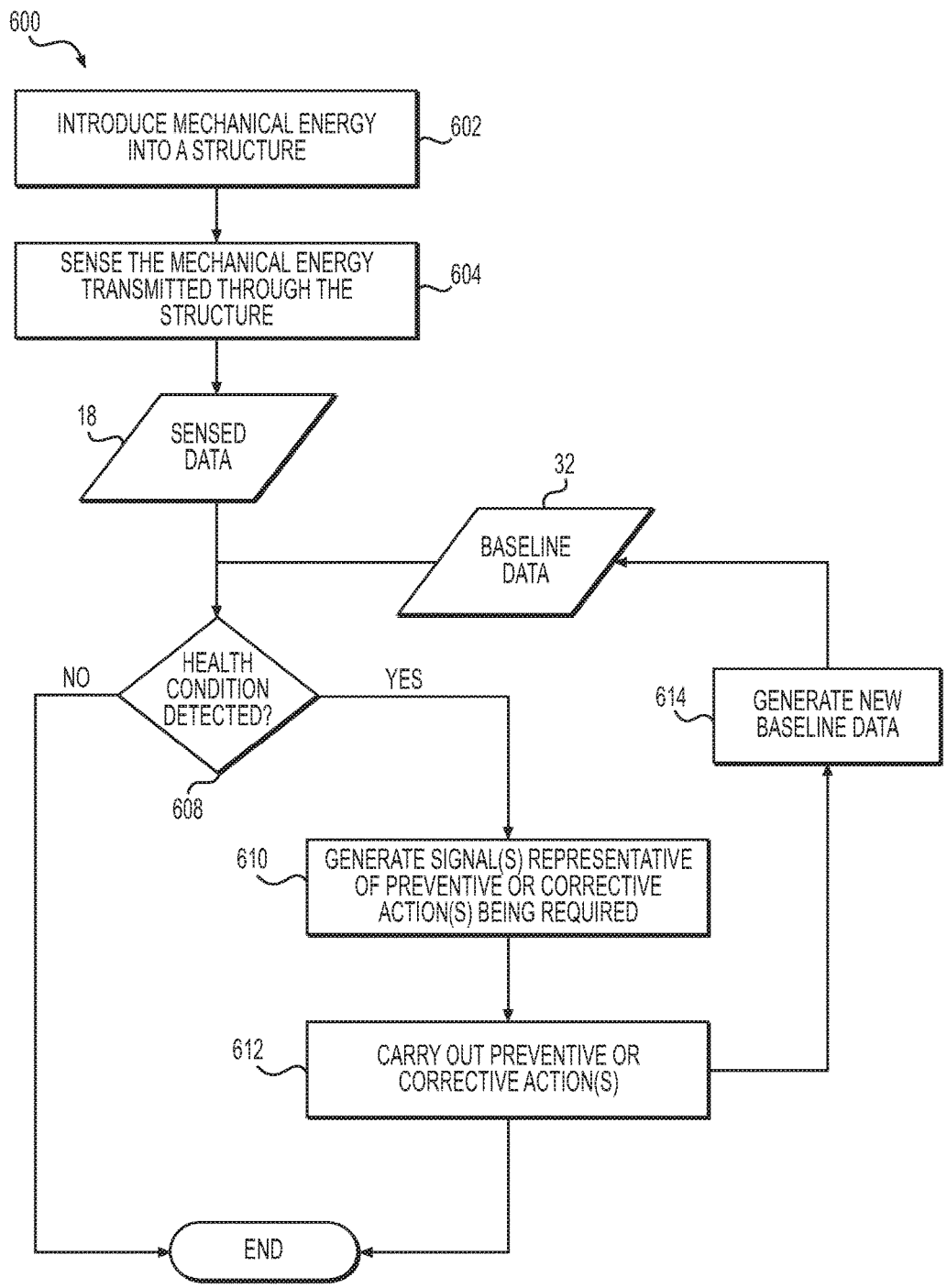
FIG. 6 shows a flowchart of an exemplary method for detecting a health condition associated with a structure.

FIG. 6 shows a flowchart of an exemplary method 600 for detecting one or more health conditions such as structural damage and/or liquid ingress in structure 14. However, it should be understood that method 600 may be used to detect health conditions in structures that may have a different configuration than the specific structures shown herein. For example, method 600 may be used in conjunction with structures that do not necessarily include sandwich portion 36. For example, method 600 may be used to detect the presence of liquid/water 50 inside sandwich portion 36 of structure 14. Method 600 may comprise: introducing mechanical energy 22 into structure 14 (see block 602); sensing the mechanical energy transmitted through structure 14 (see block 604); and determining the existence of the health condition(s) associated with structure 14 based at least in part on the sensed mechanical energy (e.g., sensed data 18) (see block 608).

Mechanical energy 22 may be introduced in first portion 38 and sensed in second portion 40. The determination of the existence of the health condition(s) may comprise comparing sensed data 18 with baseline data 32 where baseline data 32 may be associated with structure 14 being in a healthy state.

Conditioned upon no health condition being detected, method 600 may be ended as shown in FIG. 6 or, alternatively, method 600 may be repeated from block 602 as desired. Conditioned upon the health condition being detected, processing device 16 may generate one or more signals indicative that a health condition exists, indicative of the type of health condition detected and/or indicative of preventive or corrective action(s) being required (see block 610). Signals generated at block 610 may comprise an alert or message indicating the presence of one or more anomalies. For example, the one or more generated signals may comprise one or more messages indicative of a health condition without being accompanied by any suggested preventive or corrective actions. For example, the message(s) may simply indicate that liquid ingress has been detected. The message(s) may, in addition or alternatively, indicate a suggested action such as a suggested future inspection date or a modified inspection schedule based on the generated signals. For example, such modified inspection schedule may be recommended to permit monitoring of the progression of a particular health condition detected and may be based on the particular health condition detected.

For example, data representative of suggested preventive and/or corrective actions may be stored in memory 28 or may be otherwise available to processing device 16. The data representative of suggested preventive and/or corrective actions may be part of a data structure (e.g., look-up table) and may be associated with various health conditions 20 detectable by apparatus 10, 100. For example, upon detection of a particular health condition 20 such as a level of liquid ingress in structure 14, processing device 16 may retrieve data representative of one or more preventive or corrective actions associated with the specific health condition and generate appropriate signals (see block 610).

Method 600 may also comprise carrying out one or more preventive or corrective action(s) (see block 612). The carrying out of such preventive or corrective action(s) may be conducted by maintenance personnel. Alternatively, preventive or corrective action(s) may be conducted automatically or semi-automatically by apparatus 10, 100 or some other system(s) associated with (e.g., on-board or off-board) a mobile platform to which structure 14 belongs. For example, such preventive or corrective actions, may comprise the scheduling of an inspection or maintenance procedure, the activation of an alternate mode of operation of the mobile platform; and/or the carrying out of a procedure/task on the mobile platform. In various embodiments, methods 500 and 600 may be conducted during an inspection procedure when the mobile platform is not in operation or, alternatively, during operation of the mobile platform.

Depending on the type of preventive and/or corrective action(s) conducted at block 612, it may be necessary or desirable to generate new baseline data 32 to be used for future comparisons (see block 614). For example, if the preventive and/or corrective action(s) (e.g., reparation) conducted could affect the transmission of mechanical energy through (e.g., acoustic properties of) structure 14 and hence affect sensed data 18, it may be desirable to regenerate new baseline data 32 based on the repaired structure being the new healthy structure against which future comparisons would be made.

The methods (e.g., 500, 600) disclosed herein may be executed at least in part by or under the control of processing device 16. Accordingly, machine-readable instructions stored in memory 28 may be configured to cause the execution of at least portions of the methods disclosed herein. For example, such machine-readable instructions and/or data (e.g., baseline data 32) may be incorporated into one or more suitable computer programming products.

Figure 7:
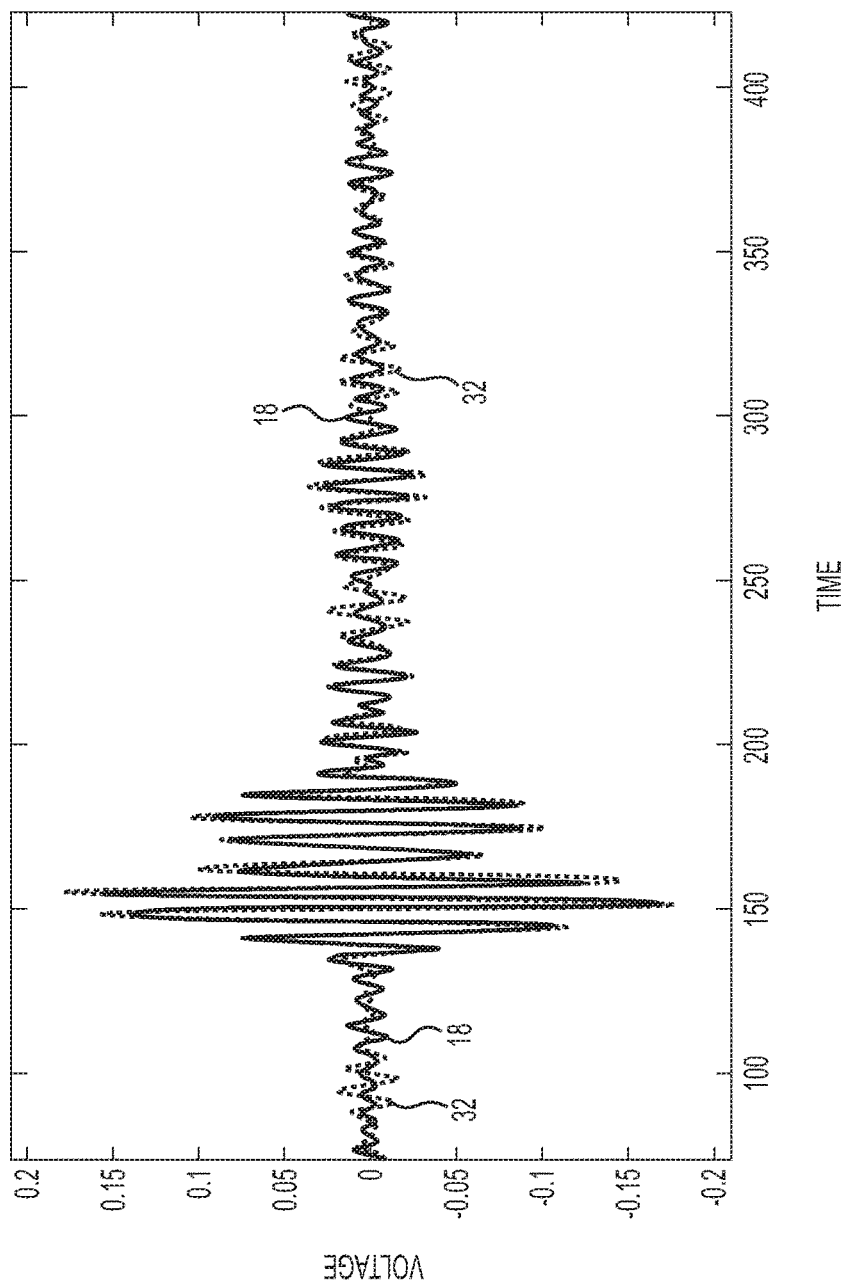
FIG. 7 shows graphical representations of an exemplary mechanical wave sensed in a structure having a undesirable health condition and a corresponding exemplary baseline mechanical wave expected when the structure is in a healthy state.

FIG. 7 shows graphical representations of sensed data 18, representative of mechanical energy sensed by sensor 12, and baseline data 32 representative of the mechanical energy expected to be sensed by sensor 12 if structure 14 is in a healthy state. FIG. 7 shows graphical representations of sensed data 18 and baseline data 32 being superimposed to graphically illustrate differences between sensed data 18 and baseline data 32. Sensed data 18 is shown as the black waveform and baseline data 32 is shown as the white waveform. Mechanical energy 22 introduced into structure 14 may be in the form of a mechanical waveform having predetermined characteristics (e.g., amplitude, frequency, duration, phase shift, time of flight, wave distortion). Differences in the characteristics of sensed data 18 and baseline data 32 may be indicative of one or more anomalies such as, for example, one or more of structural damages 47, 48, 49 and/or liquid ingress 50 in structure 14.

For example, the transmission of mechanical energy 22 through structure 14 may be affected by (i.e., modified by) the material through which mechanical energy 22 propagates. Accordingly, one or more anomalies in a portion of structure 14 may cause mechanical energy 22 to be altered, such as by causing a change in amplitude, phase, frequency, velocity or other wave propagation characteristic(s) of mechanical energy 22. As a result of the propagation of mechanical energy 22 through portions of structure 14, sensed data 18 acquired by sensor 12 will have been altered or otherwise affected by any anomalies (e.g., structural damage 47, 48, 49 and/or liquid ingress 50) within sandwich portion 36 and will therefore include information indicative of any anomalies that mechanical energy 22 would have encountered during transmission from actuator 24. For example, the presence of liquid 50 inside intermediate region 46 (see FIG. 3) of structure 14 may cause dampening of mechanical energy 22 transmitted through sandwich portion 36 and may cause a waveform defined by sensed data 18 to have different wave characteristics (e.g., lower amplitude) than a waveform defined by baseline data 32.

Processing device 16 may be configured (e.g., via machine-readable instructions stored in memory 28) to identify an anomaly such as structural damage 47, 48, 49 and/or the presence of liquid 50 in various manners. For example, processing device 16 may be configured with predefined thresholds, such as predefined values and/or ranges of amplitudes, phase shifts and/or time delays, and may be further configured to determine that sensed data 18 may be indicative of a portion of structure 14 having an anomaly in instances where a waveform represented by sensed data 18 does not satisfy the predefined thresholds, such as by having a lower amplitude, a greater phase shift, a greater time delay or the like. Alternatively or in addition, processing device 16 may be configured to compare sensed data 18 with baseline data 32 which would be anticipated to be received in instances where structure 14 is in a healthy or other known state such as by testing structure 14 in advance when it is in the healthy or otherwise known state. Accordingly, processing device 16 may be configured to compare sensed data 18 with baseline data 32 in order to determine if sensed data 18 are the same or sufficiently close to (e.g., within a predefined range of) baseline data 32 or, alternatively, if sensed data 18 differ from baseline data 32 in such a manner so as to be indicative of structure 14 having an anomaly.

Such differences indicative of an anomaly may include one or more differences in amplitude, phase shift and/or time delays. For example, the superimposition of the exemplary sensed data 18 and baseline data 32 illustrated in FIG. 7 shows that the amplitude in some portions of the waveform of sensed data 18 is lower than the amplitude of the waveform of baseline data 32. Such difference in amplitude may be representative of one or more anomalies such as one or more of damages 47, 48, 49 and/or liquid 50 being present in sandwich portion 36 of structure 14. Apparatus 10, 100 may also comprise a display (not shown) on which the illustration of FIG. 7 may be presented to an operator of processing device 16.

Figure 8:
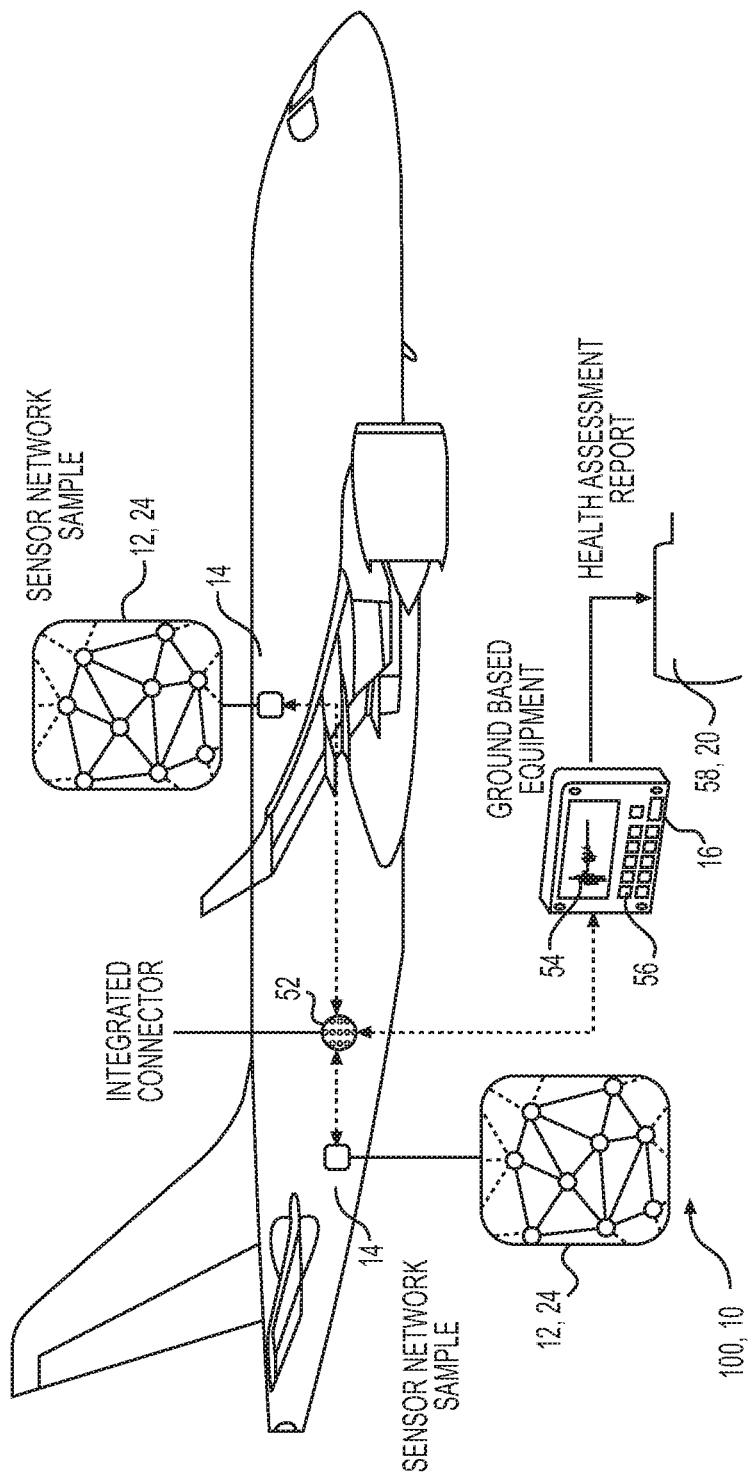
FIG. 8 shows a schematic representation of an exemplary apparatus for monitoring a structure of an aircraft.

FIG. 8 shows a schematic representation of apparatus 10, 100 used for monitoring structure 14, which may be part of an aircraft. Apparatus 10, 100 may comprise at least one sensor 12 and at least one actuator 24. Alternatively, apparatus 10, 100 may comprise a plurality of sensors 12 and a plurality of actuators 24 arranged in networks for monitoring different portions of the aircraft as illustrated in FIG. 8. Processing device 16 may be configured to communicate to sensor 12 and actuator 24 via interface 52. Interface 52 may comprise a receptacle for receiving a connector (not shown) to establish a wired connection with processing device 16. Alternatively or in addition, interface 52 may be configured to permit wireless communication between processing device 16 and sensor 12 and actuator 24.

As mentioned above, processing device 16 may be incorporated into ground-based equipment which may be portable. Processing device 16 may be configured to control the operation of actuator 24 and also receive sensed data 18 from sensor 12. Processing device 16 may comprise display 54 on which graphical representations of sensed data 18 and/or baseline data 32 may be displayed. Display 54 may instead or in addition be configured to present a suitable graphic user interface useful in operating processing device 16. Processing device 16 may also comprise one or more user-input devices 56 such as input keys, trackball, touch screen, mouse or the like, which may facilitate the operation of processing device 16.

In various embodiments, processing device 16 may be connected to sensor 12 and actuator 24 via interface 52 when the aircraft is on the ground in order to conduct an inspection of structure 14. The inspection of structure 14 may be conducted at regular intervals. Processing device 16 may be configured to output report 58, representative of at least one health condition associated with structure 14. Report 58 may, for example, be in electronic form or in printed form. Report 58, sensed data 18 and/or baseline data 32 may be transmitted to other system(s) (not shown in FIG. 8) for storage and/or further analysis. For example, the ground based equipment may serve to collect sensed data 18 while some or all analysis may be conducted on one or more other systems. Accordingly, in such embodiment the functionality of processing device 16 may be distributed between multiple processing devices.

Figure 9:
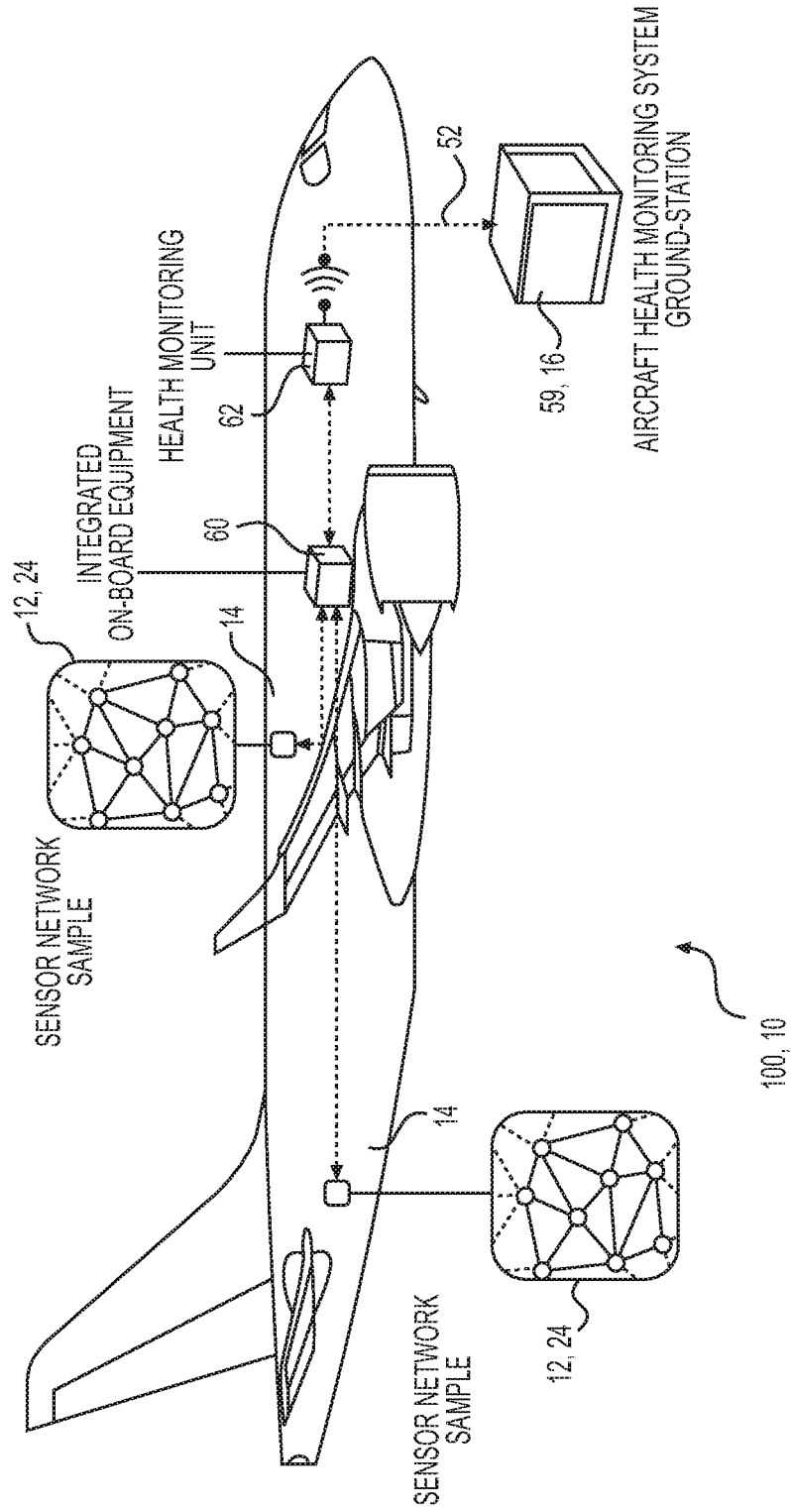
FIG. 9 shows a schematic representation of another exemplary apparatus for monitoring a structure of an aircraft.

FIG. 9 shows another schematic representation of apparatus 10, 100 used for monitoring structure 14, which may be part of an aircraft. In various embodiments, processing device 16 or part(s) thereof may, for example, be integrated into ground station 59 where sensed data 18 may be received and analysis may be conducted. For example, Apparatus 10, 100 may comprise one or more networks of sensor 12 and actuator 24 that may be used to monitor different portions of structure 14 of the aircraft. In various embodiments, the control of actuator 24 and the acquisition of sensed data 18 may be conducted automatically or semi-automatically on-board the aircraft by a health monitoring system of the aircraft and then sensed data 18 may subsequently be transmitted to ground station 59, 16 for analysis. The control of actuator 24 and the acquisition of sensed data 18 may be conducted at predetermined intervals during various phases of operation of the aircraft. For example, apparatus 10, 100 may be configured to take into account and/or compensate for disturbances in sensed data 18 that could be attributed to flight or other operational conditions of the aircraft to permit the acquisition of sensed data 18 during flight or when the aircraft is on the ground. For example, apparatus 10, 100 may be configured to compensate for vibrations, variations in environment conditions such as atmospheric pressure, temperature and/or humidity encountered during operation of the aircraft.

The transfer of sensed data 18 and optionally other data may be conducted via interface 52, which may permit wireless transfer of data from the aircraft. Apparatus 10, 100 may also comprise integrated on-board equipment 60 and health monitoring unit 62 which may control the operation of actuator 24 and receive sensed data 18 from sensor 12. For example, health monitoring unit 62 may be configured to store sensed data 18 and transmit sensed data 18 from the aircraft wirelessly and/or via a wired connection. Ground station 59 may be configured to receive sensed data 18 and optionally other data and conduct analysis. For example, the functionality of processing device 16 may be integrated into ground station 59 so that the determination of the health condition (e.g., anomaly, structural damage, liquid ingress) may be made by ground station 59. Alternatively, the functionality of processing device 16 or part(s) thereof may be integrated into integrated on-board equipment 60 and/or health monitoring unit 62 so that at least part of the determination of the health condition may be made on-board the aircraft.

Ground station 59 (e.g., including processing device 16) may be configured to receive data transmitted from the aircraft via health monitoring unit 62, store the data and optionally conduct further analysis of the data. For example, ground station 59 may receive sensed data 18 and conduct a comparison with baseline data 32 in order to determine a health condition associated with structure 14. Alternatively, the comparison of sensed data 18 with baseline data 32 may be conducted on board the aircraft and the health condition may be transmitted by health monitoring unit 62 and stored by ground station 59. In any case, ground station 59 may, in various embodiments, keep historical records of reported health conditions and optionally also sensed data 18 and also flight data (e.g., history) associated with the aircraft in order to conduct further analysis. For example, ground station 59 may be configured to identify trends in health conditions and also correlate such trends with flight data associated with the aircraft. For example, ground station 59 may be configured to correlate a particular health condition with a particular location or flight of the aircraft and also associate such health condition with the particular environmental and/or operational conditions in which the aircraft was operated. Such correlations and trend monitoring may then be used to make modifications in the design or maintenance schedule of structure 14.

While FIG. 9 only shows one aircraft from which data is transferred to ground station 59, it should be understood that ground station 59 may be configured to receive data from a plurality of aircraft, store the data and conduct further analysis of the data. For example, ground station 59 may be configured to conduct monitoring of structures on fleets of aircraft. Accordingly, ground station 59 may be configured to compare data received from different aircraft including sensed data 18, flight data and other data in order to identify trends in the health condition(s). Ground station 59 may also be configured to monitor the progression of a particular health condition associated with one or more aircraft.

Ground station 59 may comprise and/or may be in communication with a central repository that may store health monitoring data (e.g., sensed data 18) associated with a plurality of different aircraft and which may receive the health monitoring data from a plurality of ground stations 59 located remotely from one another. The central repository may also comprise one or more processing devices 16 configured to process the collected data and identify trends in the health condition(s) of a fleet of aircraft and/or a specific type of aircraft based on the accumulated data in the centralized repository.

Based on the health condition determined, ground station 59 may be configured to generate signals representative of one or more suggested preventive or corrective actions that may be required or suggested for a particular aircraft or fleet of aircraft. In various embodiments, ground station 59 may be configured to identify the particular action(s) required and schedule the required action(s). Ground station 59 may also be configured to send a notification or alert relating to the determined health condition and/or action(s) required to a pilot, operator and/or custodian of the aircraft or fleet of aircraft. Accordingly, in various embodiments, ground station 59 (and/or processing device 16) may be configured to gather and compute statistical information based on the data received from the one or more aircraft and also manage at least some aspect of the maintenance of the one or more aircraft.

The above description is meant to be exemplary only, and one skilled in the relevant arts will recognize that changes may be made to the embodiments described without departing from the scope of the invention disclosed. For example, the blocks and/or operations in the flowcharts and drawings described herein are for purposes of example only. There may be many variations to these blocks and/or operations without departing from the teachings of the present disclosure. For instance, the blocks may be performed in a differing order, or blocks may be added, deleted, or modified. The present disclosure may be embodied in other specific forms without departing from the subject matter of the claims. Also, one skilled in the relevant arts will appreciate that while the systems, devices, apparatus, methods and assemblies disclosed and shown herein may comprise a specific number of elements/components, the systems, devices apparatus, methods and assemblies could be modified to include additional or fewer of such elements/components. The present disclosure is also intended to cover and embrace all suitable changes in technology. Modifications which fall within the scope of the present invention will be apparent to those skilled in the art, in light of a review of this disclosure, and such modifications are intended to fall within the appended claims.

What is claimed is:

1. An assembly comprising:
  a structure including: a sandwich portion comprising a first layer and a second layer separated by an intermediate region; and a first portion adjacent the sandwich portion, the first portion comprising a laminate structure defined by a merging of the first layer and the second layer of the sandwich portion;
  an actuator mounted to the first portion and configured to introduce mechanical energy into the first portion of the structure for transmission into the first layer and into the second layer of the sandwich portion of the structure; and
  a sensor configured to sense the mechanical energy transmitted from the first portion along at least one of the first layer and the second layer of the sandwich portion.

2. The assembly as defined in claim 1, wherein the structure comprises a second portion mechanically coupled to the at least one of the first layer and the second layer of the sandwich portion.

3. The assembly as defined in claim 2, wherein the second portion is mechanically coupled to the first layer and to the second layer of the sandwich portion.

4. The assembly as defined in claim 2, wherein the sandwich portion defines a path along which the mechanical energy introduced into the first portion can be transmitted to the second portion.

5. The assembly as defined in claim 4, wherein the path comprises a first path comprising the first layer and a second path comprising the second layer.

6. The assembly as defined in claim 2, wherein the sandwich portion is disposed between the first portion and the second portion.

7. The assembly as defined in claim 2, wherein the first portion and the second portion are respectively disposed on different sides of the sandwich portion.

8. The assembly as defined in claim 2, wherein the sensor is configured to sense mechanical energy in the second portion.

9. The assembly as defined in claim 2, wherein the second portion comprises a monolithic structure.

10. The assembly as defined in claim 1, wherein the first portion comprises a monolithic structure.

11. The assembly as defined in claim 1, wherein the intermediate region comprises a honeycomb structure.

12. The assembly as defined in claim 1, wherein at least one of the actuator and the sensor comprises a piezoelectric transducer.

13. The assembly as defined in claim 1, wherein the actuator is configured to introduce a mechanical wave into the first portion.

14. A method for inspecting a sandwich portion of a structure comprising a first layer and a second layer separated by an intermediate region, the method comprising:
   introducing mechanical energy into a first portion of the structure adjacent the sandwich portion, the first portion comprising a laminate structure defined by a merging of the first layer and the second layer of the sandwich portion;
   sensing the mechanical energy transmitted from the first portion along at least one of the first layer and the second layer of the sandwich portion; and
   determining a health condition of the sandwich portion based on the sensed mechanical energy.

15. The method as defined in claim 14, wherein the mechanical energy is sensed in a second portion adjacent the sandwich portion and mechanically coupled to the at least one of the first layer and of the second layer.

16. The method as defined in claim 14, wherein the health condition comprises the presence of a foreign substance in the sandwich portion.

17. The method as defined in claim 14, wherein the health condition comprises water ingress in the sandwich portion.

18. The method as defined in claim 14, wherein the mechanical energy introduced comprises a mechanical wave.

19. The method as defined in claim 14, wherein the determining of the health condition comprises comparing data representative of the sensed mechanical energy with baseline data associated with the sandwich portion in a healthy state.

20. The method as defined in claim 19, wherein the determining of the health condition comprises identifying a difference in waveform characteristic between the data representative of the sensed mechanical energy and the baseline data.

21. The method as defined in claim 20, wherein the waveform characteristic includes at least one of amplitude, frequency, phase shift, time delay and wave distortion.

* * * * *